United States Patent
Levy (10) Patent No.: US 8,094,521 B2
(45) Date of Patent: Jan. 10, 2012

(54) CAREGIVER PERSONAL ALERT DEVICE

(75) Inventor: Glenn Levy, Beachwood, OH (US)

(73) Assignee: Nightingale Products LLC, Warrensville Heights, OH (US)

(*) Notice: Subject to any disclaimer, the term of this patent is extended or adjusted under 35 U.S.C. 154(b) by 633 days.

(21) Appl. No.: 12/072,537

(22) Filed: Feb. 27, 2008

(65) Prior Publication Data

US 2009/0010106 A1    Jan. 8, 2009

Related U.S. Application Data (60) Provisional application No. 60/903,872, filed on Feb. 28, 2007.

(51) Int. Cl.
  *G04B 47/00* (2006.01)
  *G04C 21/00* (2006.01)
  *G06Q 10/00* (2006.01)
(52) U.S. Cl. .............. 368/10; 368/73; 705/2; 705/7.13
(58) Field of Classification Search .............. 368/10, 368/41, 72–74, 250–251; 705/2, 3, 9
  See application file for complete search history.

(56) References Cited

U.S. PATENT DOCUMENTS

| | | | |
|---|---|---|---|
| RE32,655 E | 4/1988 | Levine | |
| 6,335,907 B1 | 1/2002 | Momich et al. | |
| 6,640,212 B1* | 10/2003 | Rosse | 705/9 |
| 6,714,913 B2* | 3/2004 | Brandt et al. | 705/2 |
| 6,934,220 B1 | 8/2005 | Cruitt et al. | |
| 6,961,285 B2 | 11/2005 | Niemiec et al. | |
| 7,587,329 B2* | 9/2009 | Thompson et al. | 705/9 |
| 2003/0139955 A1* | 7/2003 | Kirii et al. | 705/7 |
| 2003/0149598 A1* | 8/2003 | Santoso et al. | 705/2 |
| 2004/0243444 A1* | 12/2004 | Steusloff et al. | 705/2 |
| 2005/0086082 A1* | 4/2005 | Braunstein et al. | 705/2 |
| 2005/0240441 A1* | 10/2005 | Suzuki et al. | 705/2 |
| 2005/0254348 A1 | 11/2005 | Niemiec et al. | |
| 2006/0053035 A1* | 3/2006 | Eisenberg | 705/2 |
| 2006/0074740 A1* | 4/2006 | Garcia et al. | 705/9 |
| 2006/0106641 A1* | 5/2006 | Bartsch et al. | 705/2 |
| 2006/0163360 A1* | 7/2006 | Steusloff et al. | 235/472.02 |
| 2007/0255348 A1* | 11/2007 | Holtzclaw | 607/60 |
| 2008/0139898 A1* | 6/2008 | Johnson et al. | 600/301 |
| 2008/0164998 A1* | 7/2008 | Scherpbier et al. | 340/539.13 |
| 2009/0010106 A1* | 1/2009 | Levy | 368/10 |
| 2009/0089092 A1* | 4/2009 | Johnson et al. | 705/2 |
| 2009/0275807 A1* | 11/2009 | Sitzman et al. | 600/301 |
| 2009/0313046 A1* | 12/2009 | Badgett et al. | 705/3 |
| 2010/0004948 A1* | 1/2010 | Toomey et al. | 705/3 |
| 2010/0134609 A1* | 6/2010 | Johnson | 348/77 |

* cited by examiner

*Primary Examiner* — Vit Miska
(74) *Attorney, Agent, or Firm* — Fay Sharpe LLP

(57) ABSTRACT

The present invention relates to a portable caregiver personal alert device to facilitate the improvement in the delivery of bedside patient care. The device assists caregivers in ensuring time-sensitive tasks are performed within a specific time frame and in a specific sequence to ensure efficiency, compliance with standard of care or regulation and patient comfort. The device of the present invention comprises a display, a microprocessor that monitors various tasks for multiple patients, and at least one user input feature and at least one alarm, capable of alerting a caregiver when it is time to perform the task. The device preferably includes various functions such as a bed assignment mode, a task mode for choosing applicable tasks associated with the needs of one or more bed numbers, and at least one clock for coordinating a plurality of alarms to one or more corresponding bed number and associated task.

19 Claims, 8 Drawing Sheets

CAREGIVER PERSONAL ALERT DEVICE

This application claims the benefit of U.S. Provisional Application No. 60/903872, filed Mar. 28, 2007.

BACKGROUND

The present invention relates to a medical device. More particularly it relates to a programmable device capable of maintaining alerts for various time-sensitive interventions for associated patients. It finds particular application in conjunction with bedside care of patients and will be described with particular reference thereto. However, it is to be appreciated that the present exemplary embodiment is also amenable to other like applications.

Recently there has been a convergence of forces bringing to light an urgent need for an improvement in the delivery of bedside care to patients. One such force has been the proliferation of the practice of evidence based medicine. The practice of evidence based medicine determines what "best practice" protocols, represented by various time-sensitive interventions, will produce the best possible patient care, such as what to do, when to do it, and what sequence to do it in. Over the last decade, evidence based practice has grown significantly due to the vast advancements in information technology. Another emerging force is the national rise in public distrust for healthcare due to mistakes made by caregivers resulting in slow rates of recovery, patient discomfort and even patient death. The final force is due to increases in public access to quality, satisfaction and safety data, which are driving up healthcare quality standards. The public can now easily view hospital reviews, ratings, and comparisons, making it incredibly easy for individuals to determine which healthcare facility provides the best patient care. Access to information has caused the public to demand improvements because people are dissatisfied and most importantly, people are dying that could have lived.

While the standards for healthcare are rapidly increasing, the healthcare facilities are experiencing a manpower shortage, particularly with those who provide bedside care. Caregivers have to take care of many more patients than before, while patients are getting older, sicker, and are requiring more attention.

Therefore, there exists an urgent need for a device that assists bedside caregivers in timely executing the growing number of time-sensitive interventions, at the right time and in the right sequence, for the purpose of optimizing the quality of patient outcomes, promoting cost effectiveness and improving customer satisfaction.

Electronic calendar/appointments are well known in the art, such as U.S. Pat. Reissue No. 32,655, which teaches of an electronic schedule calendar and diary for storing a plurality of future calendar appointments and events for each of a plurality of date interval periods. However, such electronic calendars contain no convenient way to program alerts tied to specific bed assignments and do not allow for discrete alarms for preprogrammed time sensitive interventions discusses above. U.S. Pat. No. 6,934,220 discloses a programmable medical alert device that can be used to program multiple events, such as medication schedules. Each programmed event will signal an alarm at the same time of day each at which the alarm was originally set. However, such a device is not adaptable to a broad range of functions, such as setting numerous alerts for a number of different bed assignments corresponding to needed time sensitive interventions. Further, U.S. Pat. No. 6,961,285 teaches a system and process for assisting patients with medication compliance including a medication package with a portable medication monitor to provide support to the patient in taking medication as directed. However, similar to the above mentioned patents, this system does not disclose the various functionalities of the present invention.

Therefore, a portable device has yet to be developed for the use of a caregiver that facilitates improvements in bedside care in healthcare institutions by providing an easy and efficient way for a caregiver to monitor the needs of multiple patients simultaneously using discreet alerts programmed to remind caregivers when needed care is required. Such a device would greatly improve individual patient care, patient satisfaction, and patient rate of recovery and, not only save healthcare facilities money, but also save lives.

BRIEF DESCRIPTION

The present invention relates to a portable device for coordinating a plurality of tasks with corresponding alarms to alert a caregiver. The device comprises a display, a microprocessor capable of monitoring a plurality of functions dedicated to assist the caregiver in managing a plurality of tasks for multiple patients, at least one user input feature, and at least one alarm capable of alerting said caregiver when it is time to perform the task. The device may include various functions such as a bed assignment mode, wherein a caregiver can designate bed numbers, a task mode with at least one pre-programmed task, which may be associated with one or more of said bed numbers, and at least one time clock capable of coordinating a plurality of alarms to one or more corresponding bed number and associated task.

In another aspect of the invention, the portable device is adapted for use by a nursing team. The nursing team device is capable of coordinating a plurality of time-sensitive tasks with corresponding discreet alarms to alert a caregiver and includes a display, a microprocessor capable of monitoring a plurality of functions dedicated to assist said caregiver in managing a plurality of time-sensitive tasks for multiple patients, at least one user input feature, and at least one alarm capable of alerting said caregiver when it is time to perform the task. A team leader uses the nursing team device to assign team member duties by either inputting assignments directly onto said team member devices, or by putting the assignments on a central site where each team member may download their assigned duties directly onto the device.

BRIEF DESCRIPTION OF THE DRAWINGS

The invention will now be described by way of example only, with reference to the accompanying drawings, in which.

DETAILED DESCRIPTION

Figure 1:
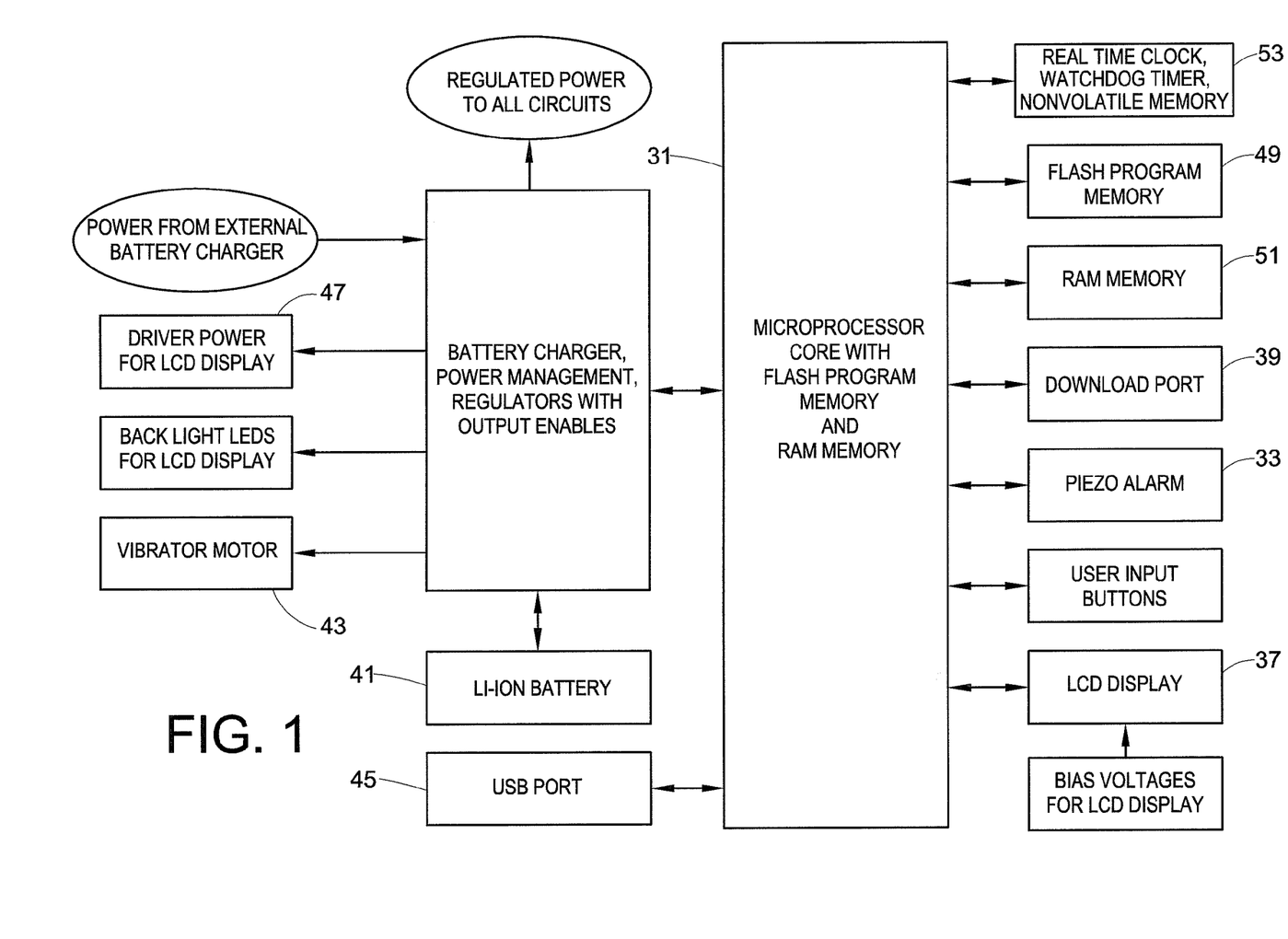
FIG. 1 is a block diagram representing the device with input buttons.
Figure 2:
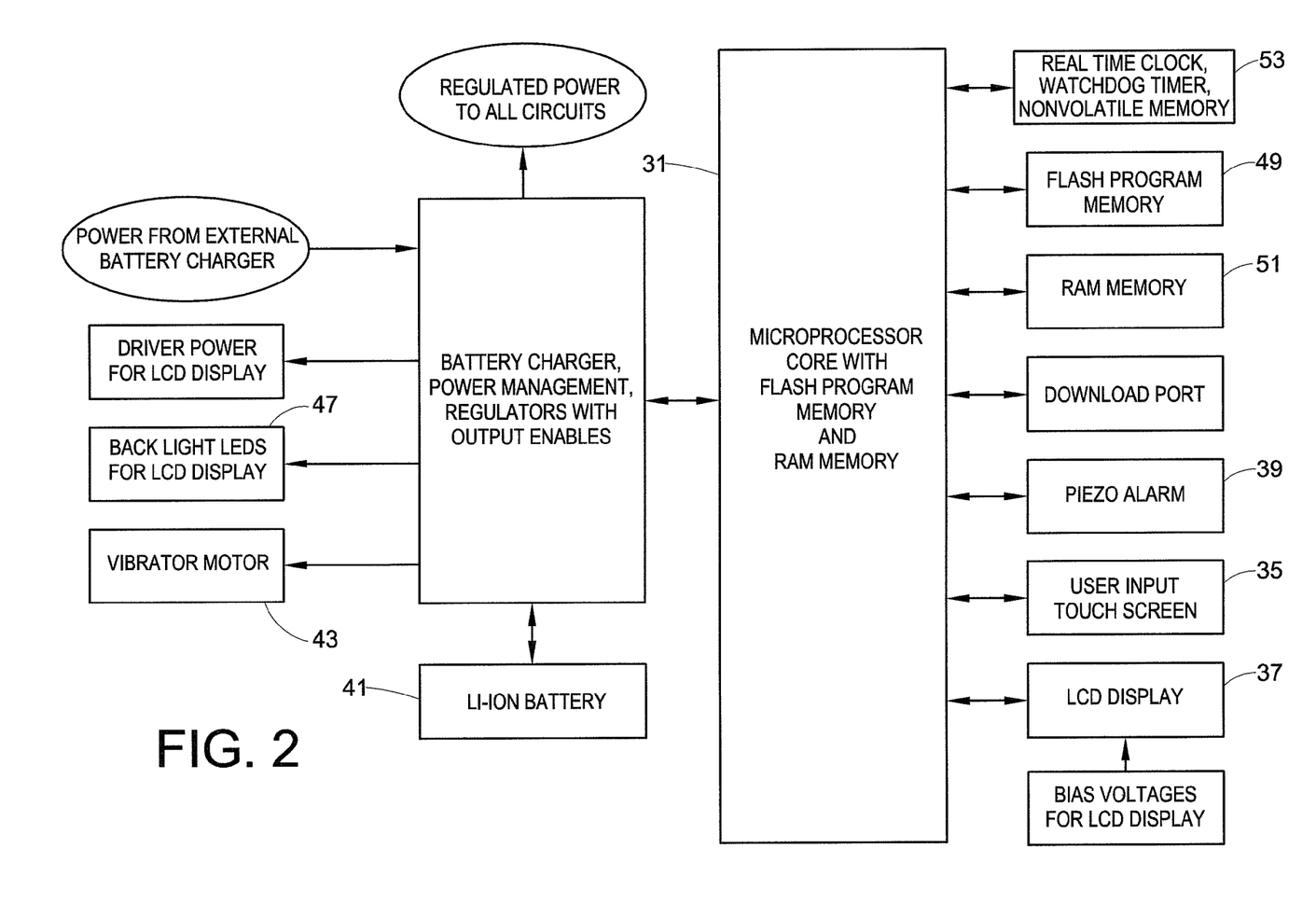
FIG. 2 is a block diagram representing the device with a user input touch screen display.

This application incorporates by reference the description set forth in provisional patent application No. 60/903,872, filed Feb. 26, 2007. Referring now to the drawings wherein the showings are for purposes of illustrating the exemplary embodiments only and not for purposes of limiting the claimed subject matter, FIGS. 1 and 2 provide block diagrams representing two embodiments of the functionality of the Caregiver Personal Alert Device of the present invention. The device includes a microprocessor core 31, which provides a display 37 and interface capabilities. The microprocessor core 31 preferably comprises memory to store information useful for a caregiver's record keeping. Preferably, the device comprises both Flash Program Memory 49 and RAM Memory 51; however, any form of memory known in the art may be used. The device will store and display each alert programmed into the device and the actual time each alert was acknowledged by a caregiver for reference purposes. A caregiver can review daily actives on a device to determine exactly when the alert for a task was acknowledged. For example, if, while a caregiver is attending to a critical patient needing the caregiver's undivided attention, alert(s) goes off concerning other patients, a caregiver can consult his or her device and review which alerts went off and what bed assignments need attention. Preferably, the alert information will remain stored on the device until a user manually clears the memory and/or downloads the information onto a computer for indefinite storage and reference.

The microprocessor core 31 may include both input and output capabilities. The input capabilities of the device may include user input pushbuttons 33 to assist a caregiver in programming the device to his or her specific needs. In another embodiment of the present invention, the device comprises a user input touch screen 35 along with or instead of pushbuttons. In yet another embodiment, the user inputs information audibly, by speaking commands into the device. The output capabilities of the device preferably include a display 37 to visually output information to a caregiver. The display 37 is preferably an LCD display 37 with backlight LEDs 47; however, any display known in the art may be used. The output capabilities may also preferably include an alarm 39 to alert a caregiver a pre-programmed task is due. The alarm may alert the caregiver visually in conjunction with the display, audibly, and/or through a vibration. Preferably the alarm 39 is a Piezo alarm. The alarm 39 may be set for a specific time of day using a real-time clock 35m which may use standard or military time, or it may be set for a specific length of time, preferably in one minute intervals from one minute to twenty-four hours. A caregiver may also set an "ad hoc" alert, wherein at any time the caregiver can instantly prompt the device to alert the user at three (3), five (5), or ten (10) minutes. The "ad hoc" alert function may be modified to provide for any desired length of time.

Optionally, the device may contain a USB port 45 to assist in the download of information off and onto said device. For example, a user may download daily assignments or reminders from a central site that automatically programs the caregiver's bed assignments. Similarly, a caregiver may upload his or her daily stored record of patient care activities onto a computer database for indefinite storage. Such records would be very useful to health care facilities, particularly to rebut a claim of negligent or lack of care.

The device is preferably powered through batteries 41, and more preferably rechargeable batteries. Optimally, the battery 41 is a Li-Ion battery capable of recharging through a 120 v electrical outlet. The battery provides regulated power to all circuits, namely it powers the LCD display 37, the backlight or the LEDs 47 for LCD display 37 and the vibrator motor 43.

Figure 3:
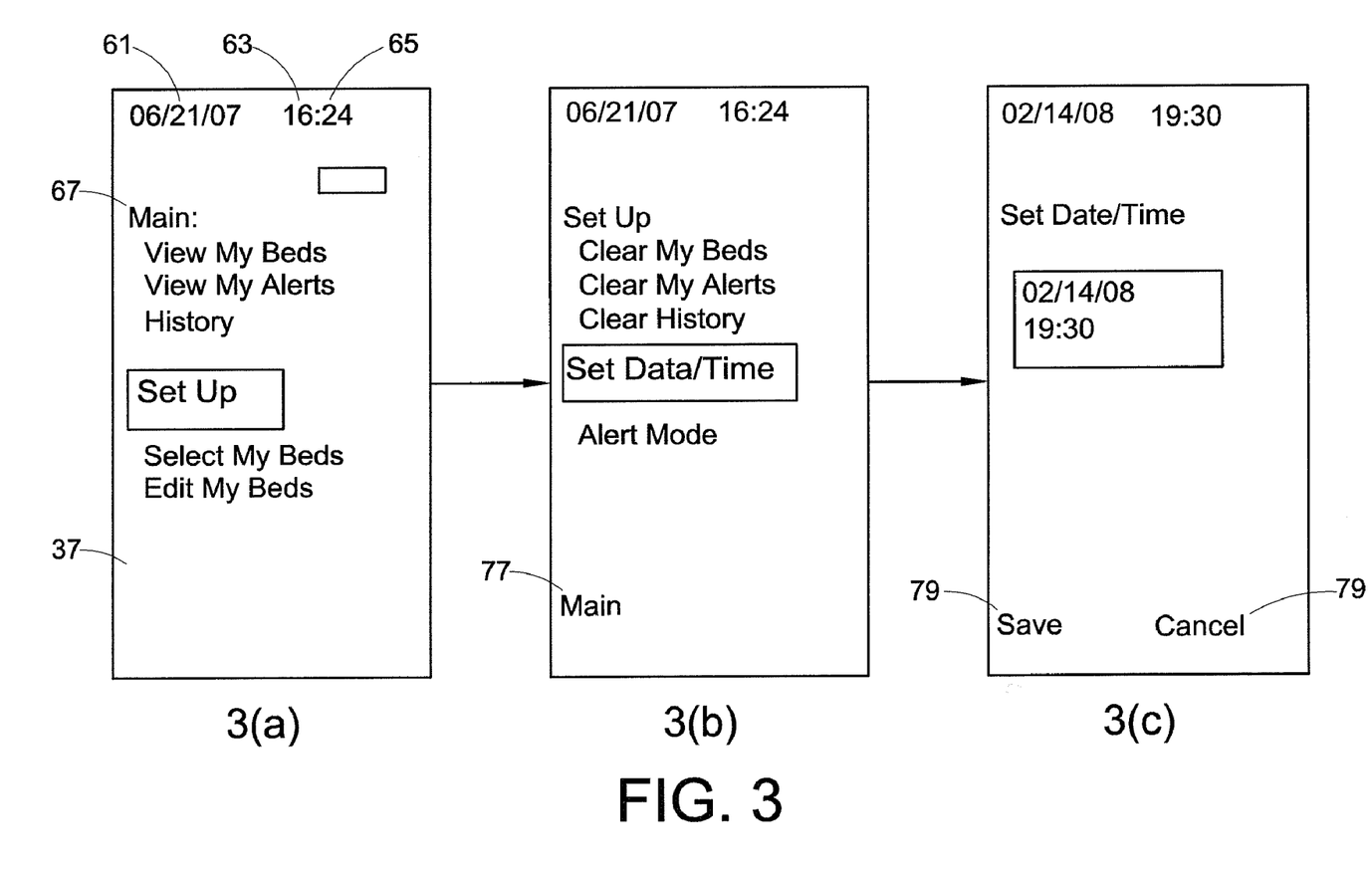
FIG. 3 is a schematic representation depicting the process of setting the time and/or date for the device.

FIGS. 3-7 represent exemplary embodiments of some of the possible functionalities of the device; however, a device may include variations that are either different or are not depicted in the figures. Referring now to FIG. 3, the process of setting the date and/or time is displayed. FIG. 3(a) displays one embodiment of a "Main Menu" screen, wherein the date 61, time 63, battery life 65, and main menu 67 are displayed. The "Main Menu" screen may be reached at any time by selecting "Main" 77 when it appears at the bottom of the screen. Preferably, the "Main Menu" screen is the default home screen until a user programs bed assignments. Upon assigning beds; however, the preferable default screen become the "View My Beds" screen. Preferably, the date 61, time 63 and battery life 65 are continuously displayed at the top of each screen. The battery life 65 displays the time left on the battery and may emit an alert when the battery life falls to below 30 minutes. The low battery alert may be adjusted by a user as desired. The main menu 67 comprises a list of possible functions, including "View My Beds," "View My Alerts," "History," "Select My Beds," "Edit My Beds" and "Setup." This list is not exhaustive of the possible functions, and can be modified to suit a user's needs.

As shown in FIG. 3(a), the function "Setup" is highlighted. Selecting "Setup" takes the user to the "Setup" screen comprising a list of options including "Clear My Beds," "Clear My Alerts," "Clear History," "Set Date/Time" and "Alert Mode." As stated above, this list is not exhaustive of the possible functions in the "Setup" screen, and it may be modified to suit a caregiver's needs. Selecting the function "Clear My Beds" clears any bed assignments that have been previously made, and the alerts corresponding therewith. The function "Clear My Alerts" clears any alerts that may have been set, whether they were assigned to a specific bed, or just a general alert; however the bed assignments remain intact. The selection of "Clear History" clears any stored history on the device since the previous time it was cleared. The selection of "Alert Mode" will take a user to a screen listing the possible types of alerts, such as vibrate, beep, or visual and the user can select which type, or any combination, of the alerts they wish to use. Selection of the function "Set Date/Time" will take a user to another screen shown in 3(c) titled "Set Date/Time." From this screen a user can set the current time and date or any time and date they choose. By pressing "Save" 79 the changes will be saved and the user may either return to the "View My Beds" screen, the "Main" screen, or any other designated default screen. By pressing "Cancel" 75, the information will not be saved and the user will be returned to the "View My Beds," "Main," or other designated default screen. Once the time and/or date is modified and saved, this modification will appear at the top of every screen in the date location 61 and the time location 63.

Figure 4:
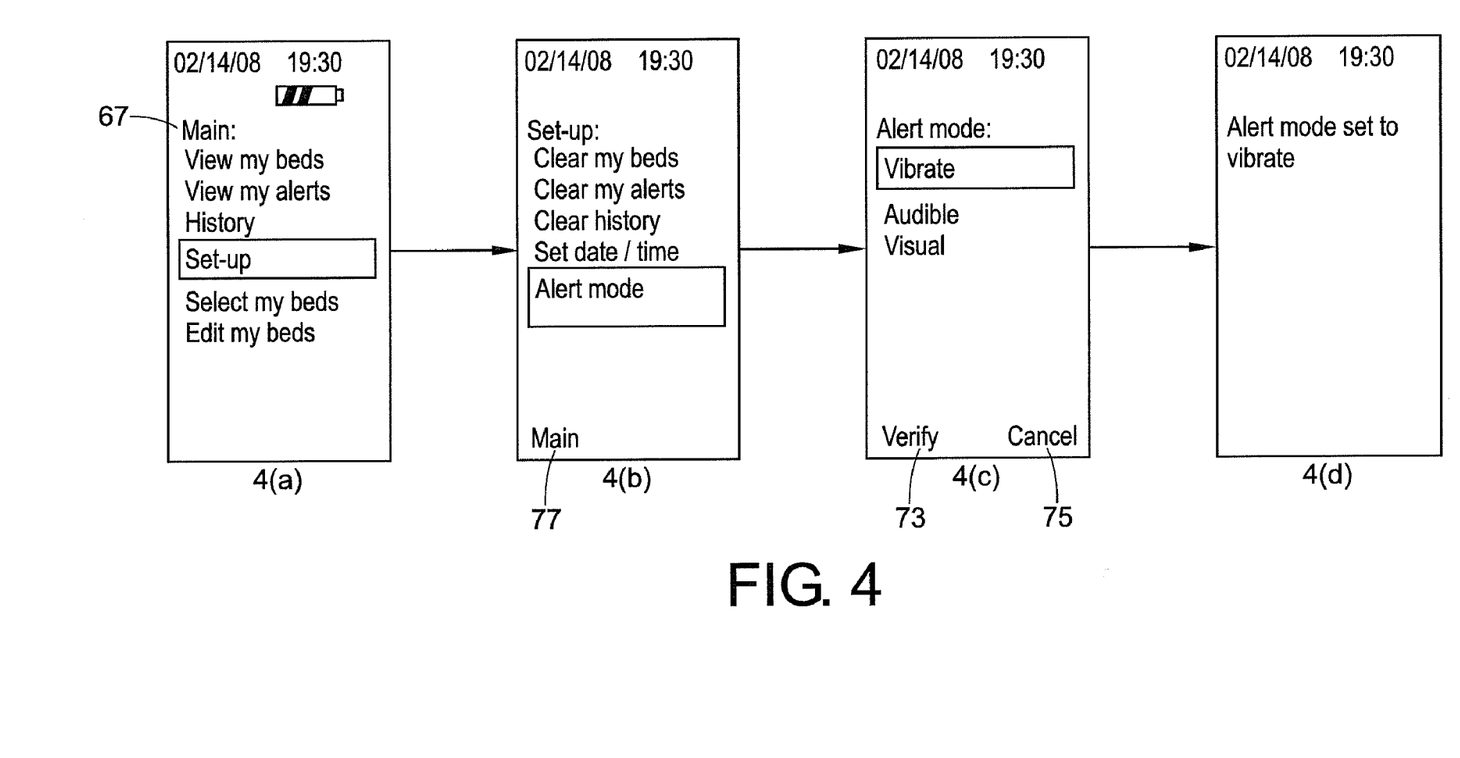
FIG. 4 is a schematic representation depicting the process of setting up the alert mode.

FIG. 4 represents one embodiment of the process a user goes through to set the alert mode for the device, i.e. audio, visual, vibrate, etc. With reference to FIG. 4(a), the "Main Menu" screen is provided displaying the main menu 67, in which the function "Setup" is highlighted by a user. The "Setup" function brings a user to the "Setup" screen similar to that in FIG. 4(b). The selection of "Set Alert Mode" brings a user to the "Set Alert Mode" screen shown in FIG. 4(c). The "Set Alert Mode" screen lists the various types of alerts a user may choose, such as vibrate, audible and visual, or any combination of the three modes. Preferably if no alert has been selected, vibrate mode is the default. However, once an alert has been selected, it remains the alert until a user chooses differently. The alert types may be modified to other alerts known to those skilled in the art. After selecting an alert type, the user must select "Verify" at the bottom of the screen to move to a confirmation screen such as that in FIG. 4(d). The user will be able to view the new alert mode and may select "Main" to return to the main menu 67. Selecting "Cancel" 75 erases any changes to the alert and returns the user to the "Main Menu" screen or any other screen designated as the default screen.

Figure 5:
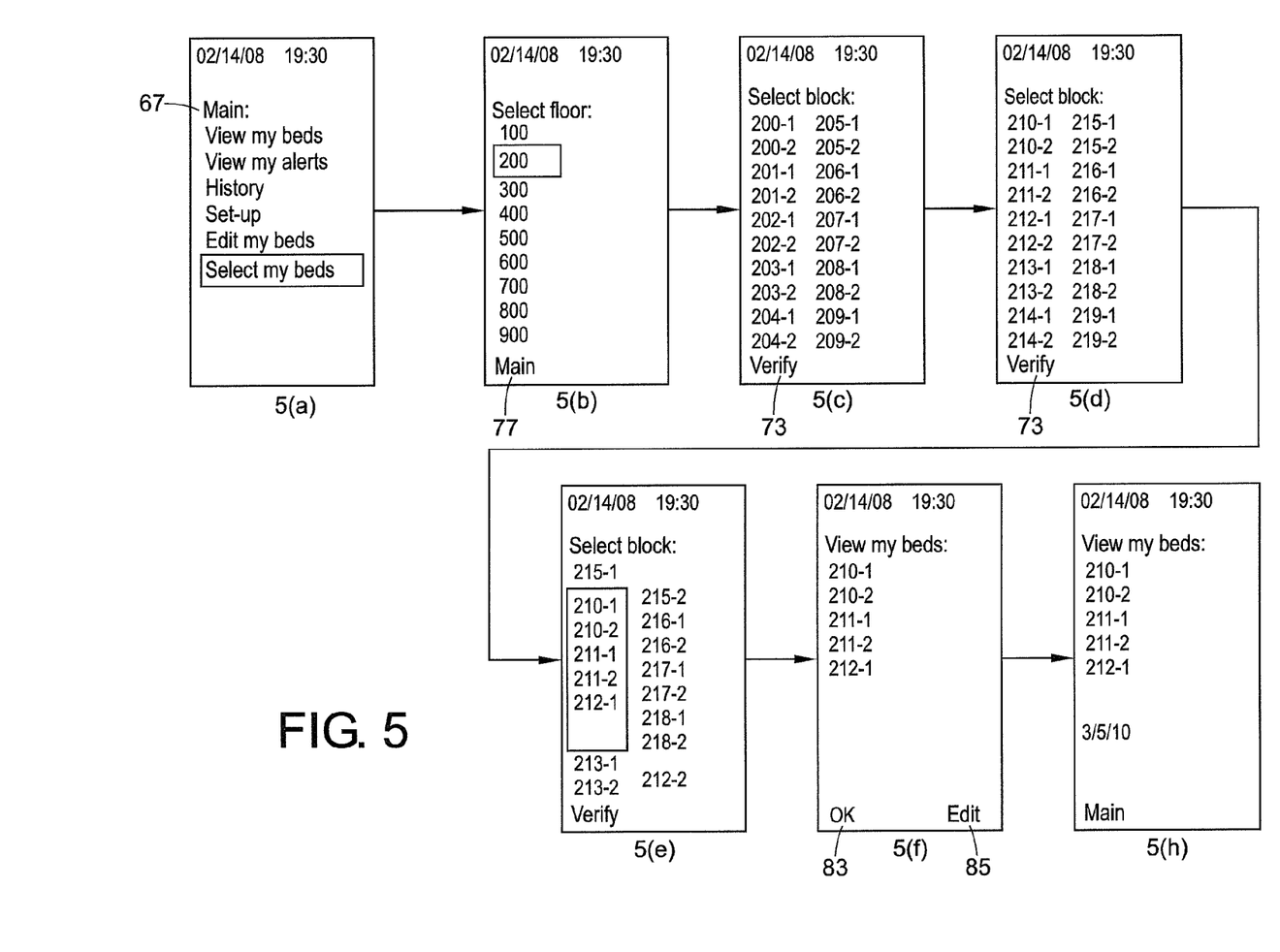
FIG. 5 is a schematic representation of the process of selecting bed assignments.

Referring now to FIG. 5, one embodiment of the process for selecting beds is provided. FIG. 5(a) displays a main menu 67 similar to those shown in FIGS. 4(a) and 3(a). Upon selecting the function "Select My Beds," a user is prompted to select a floor from a list of the possible floors in the user's health facility. FIG. 5(b) displays floors 1-9, designated by numbers 100-900. The numbers of floors may be adjusted depending of the number of floors in a particular facility. Once a user has selected the floor, the user is prompted to select a block of beds. FIGS. 5(c) and 5(d) display various room numbers from 201 to 219; however, room numbers may be customized to provide for a facilities' specific design. When a room number has multiple beds, the bed numbers are designated by dash and a 1 or a 2 after the room number, indicating the bed by the door or the window. Private rooms are designated by a 1 after the room number. Preferably, a user can scroll though different screens of blocks of bed numbers or even more preferably a user may scroll through the blocks of bed numbers without changing screens. However, depending on the size of a facility, it may be desirable to have options for a user to select to expedite them to a certain block of beds, such as "Block 200-220," Block 221-240," and so on. To verify bed selections, the user must select "Verify" 73 to save the bed selections. By pressing "Verify" 73, the user is prompted to the screen "View My Beds," where the selected bed numbers are displayed and a user is prompted to select "OK" 83 or "Edit" 85. Selecting "OK" 83 will take the user to the "View My Beds," now the default home screen as discussed above. Selecting "Edit" 85 will return the user to the "Select Floor" screen shown in FIG. 5(b), and the user may re-select bed assignments.

Figure 6:
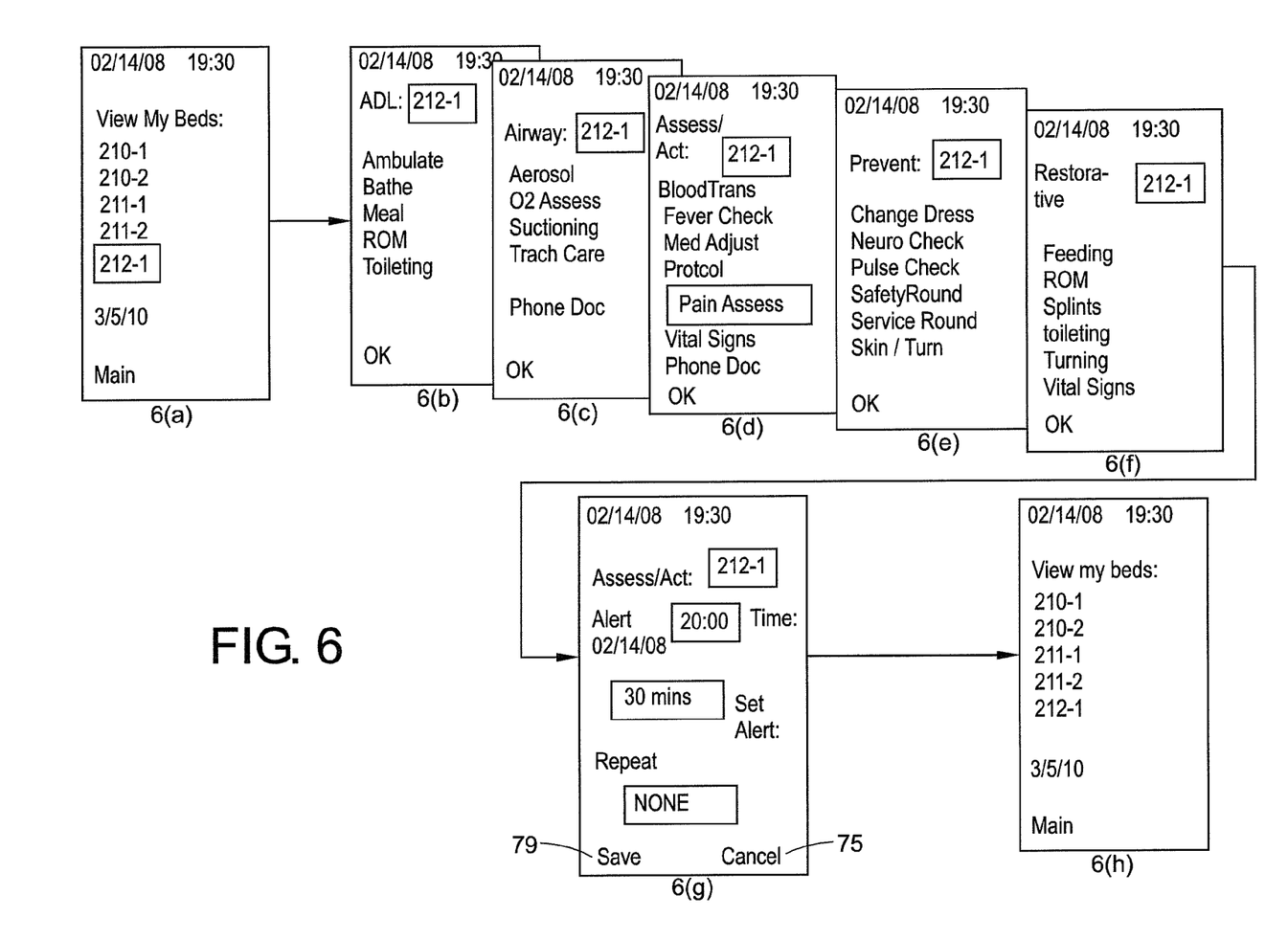
FIG. 6 is a schematic representation of the process of setting an alert for a particular assigned bed.

FIG. 6 displays one embodiment for setting an alert to a specific bed number. From the home screen in FIG. 6(a) displaying a list of the assigned beds, a user may select the bed in which to assign an alert. The home screen may also display 3/5/10 at the bottom of the screen in which a user can set the "ad hoc" alerts referred to above. Upon selecting a bed, the user may scroll through various alert category screens displaying corresponding task lists relating to the type of assistance needed. Such alert category screens include for example, activities of daily living ("ADL"), airway, assessment/act, preventative and restoratives. The "ADL" screen (FIG. 6(b)) preferably includes a list of time sensitive activities for daily living including, but not limited to, ambulate, bathe, meal, ROM, and toileting. The "airway" screen (FIG. 6(c)) preferably includes time sensitive tasks such as aerosol, OS assess, suctioning, tracheal care and phone doctor. Selection of "phone doctor" allows a user to set one or more alerts to call a doctor. For example, a caregiver may set the "phone doctor" alert as a reminder to call a patient's physician at various times through a patient's treatment. The "assess/act" screen (FIG. 6(d)) preferably comprises a list of time-sensitive tasks such as, by way of example, blood transfusion, fever check, medicine adjustment, pain assessment, protocol, vital signs and phone doctor. The "prevent" screen preferably includes time-sensitive tasks such as, by way of example, change dressing, neuro check, pulse check, safety round, service round, and skin turn. The "restorative" screen (FIG. 6(f)) preferably includes various time sensitive tasks including, by way of example, feeding, ROM, splints, toileting, turning, and vital signs.

In the embodiment of the present invention depicted in FIG. 6, the pain assessment task was selected on the "access/act" screen was selected. This selection (as with the selection of any other task) brings a caregiver to a screen where a user may set the necessary alert as shown in FIG. 6(g). Preferably, the user may then set the time the alert is to be activated and how many times, if any, the alert is to be repeated, up to and including four repeats. For example, as shown in FIG. 6(g), at the time the alert was set, the time displayed 19:30 hours. The alert was set for 30 minutes; therefore, the alert time was set for 20:00 hours. The user may then select "Save" 79 to save the alert, or "Cancel" 75 to discard the changes and return to the "Main Menu" screen, the "View My Beds" screen, or any other screen designated as the default. The device is preferably capable of simultaneously tracking up to ten tasks for up to fifteen patient locations; however this number can be increased if such need arises.

Figure 7:
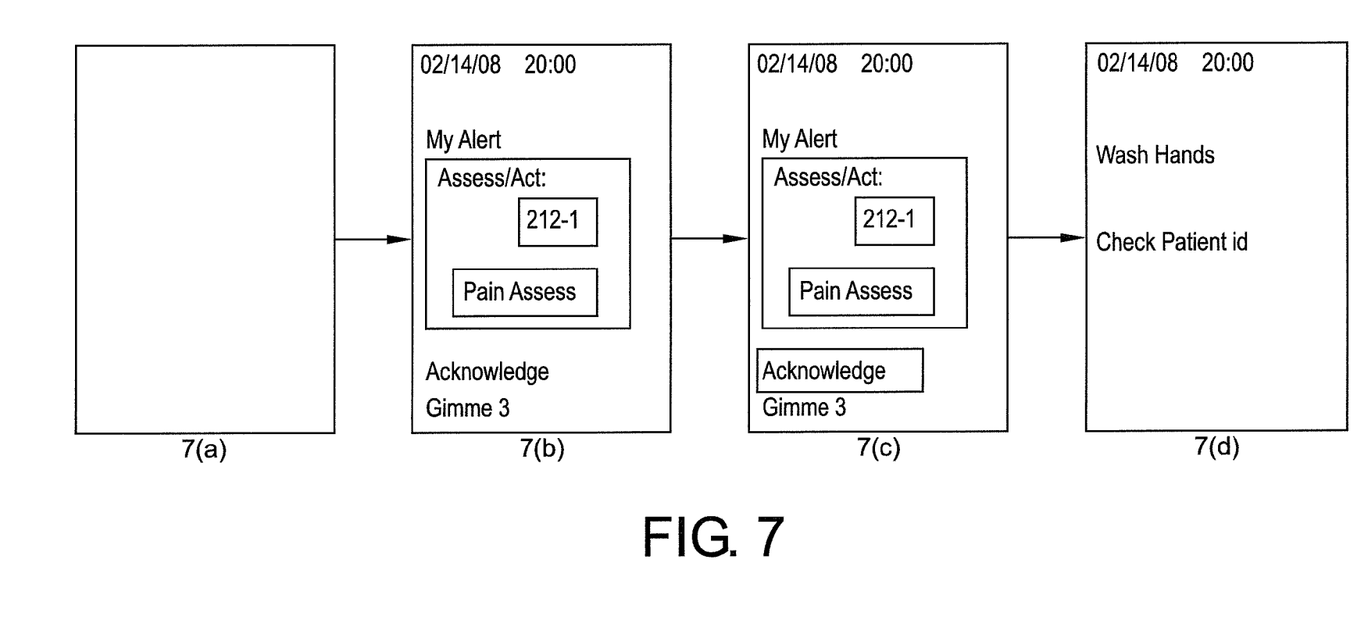
FIG. 7 is a schematic representation of the process of acknowledging an alert.

FIG. 7 displays one embodiment of the process of acknowledging an alert. From a sleeping mode, used to conserve power when the device is not in use, as seen in FIG. 7(a), an alert triggers the display of "My Alert" screen shown in FIG. 7(b). In "My Alert" the bed number flashes and the specific alert is displayed on the screen. The user has the option of selecting "Acknowledge," to tend to the matter immediately, or "Gimme 3," to set a three minute reminder. The selection of "Acknowledge" will prompt the display "Wash Hands" and "Check Patient ID" to remind the caregiver to perform these safety steps before rendering care.

Although not specifically depicted in the drawings, the device of the present invention includes functionality providing benefits beyond that are illustrated above. For example, when a patient moves beds, it is possible to transfer programmed alerts to another bed, so as not to lose a patients required task list simply because the patient moved. In another embodiment, the device may incorporate a wireless communication with mattress pads that sense when a patient may be trying to ambulate, and is at risk of falling or has fallen out of bed. The device and mattress pads would be synchronized so that the patient's caregiver would be alerted when not in ear shot of the mattress pad local alarm, and could possible prevent an injury or arrive on the scene immediately to render assistance to a patient who has fallen to prevent further injury.

In yet another embodiment, the device may interface with electronic medical record systems for documentation of execution of evidence-based best practice. Alternatively, the device may have video capability to download educational and in-service demonstrations related to skill and competency building of delivery of bedside care. Further, the device may incorporate MP3 capabilities for the purpose of listening to music and/or instructions.

In another embodiment, the device is used for team caregiving, e.g. RN-LPN-STNA team, to coordinate the duties of each caregiver on a team. In this embodiment, a team leader can input assignments for completing tasks directly onto a team member's device, or preferably, the assignments may be downloaded off a designated central site. In another embodiment of the device used for team care giving, there is wireless connectivity among each device in a team enabling each member to signal for assistance from another team member in a remote location on the unit, such as when a STNA identifies that intervention by their RN supervisor is urgently needed. In yet another embodiment, the device uses a USB to synchronize the caregiving team using a program that can preset alerts for the team's panel of patients.

Figure 8:
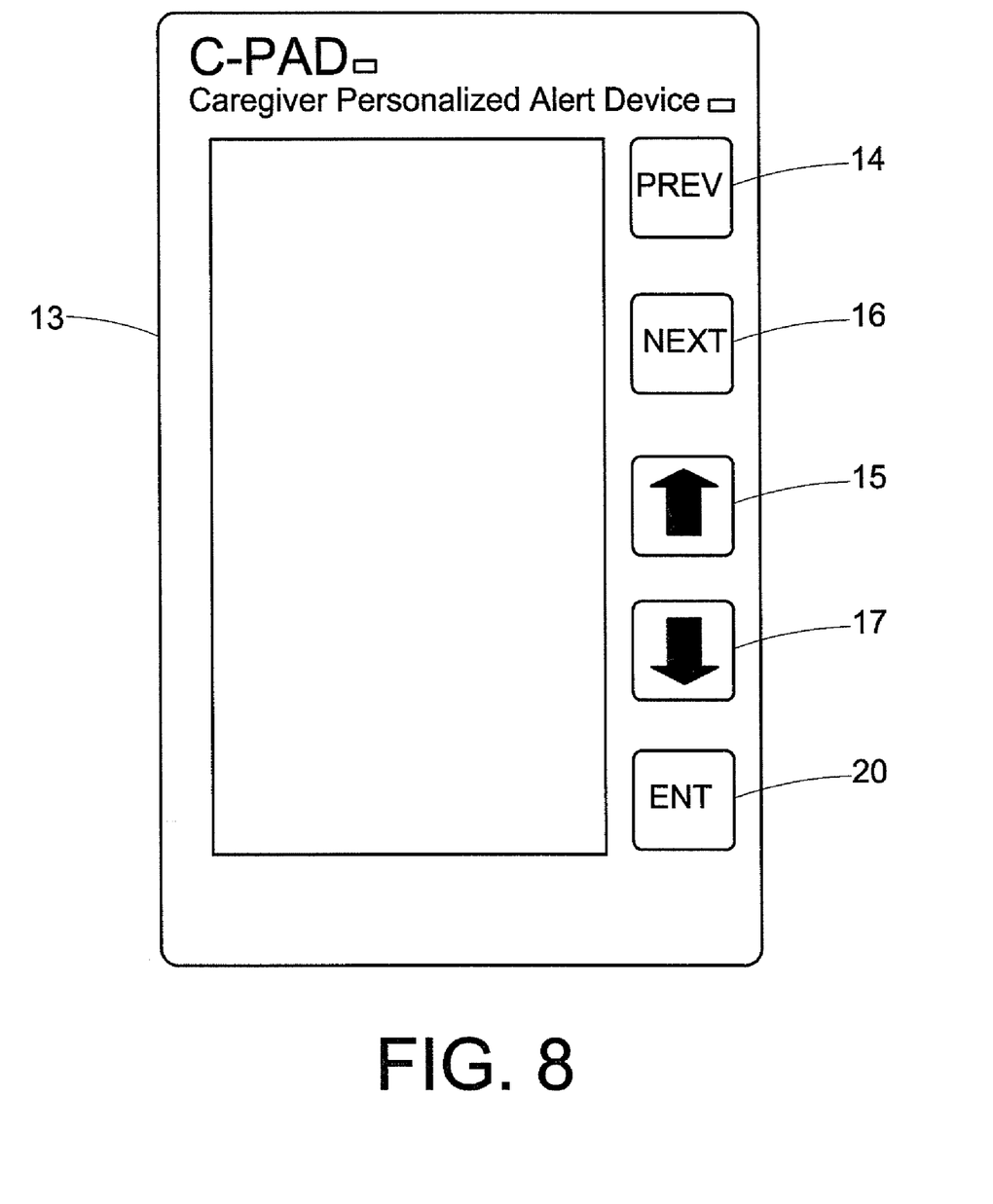
FIG. 8 is a front view of one embodiment of the device pushbutton overlay.

Referring now to FIG. 8, an overlay 12 for the device is provided that may be incorporated with the device to essentially package the present invention and make it more user friendly. The overlay 12 depicted in FIG. 8 encompasses pushbuttons; however, it is to be understood that the device may include other methods of user input known in the art, such as through a touch-screen display. The overlay 12 may be a hard protective covering for the device, an adhesive covering for direct application to a plastic enclosure of the device or any other form known to those skilled in the art. The overlay 12 depicted in FIG. 8 includes 5 pushbuttons; however any number of buttons may be used. In this embodiment of the present invention, the five buttons comprise a previous button 14, a "next" button 16, an "up" button 18 comprising an upward facing arrow, a "down" button 17 comprising a downward facing arrow and an "enter" button 20. The button locations may be pillowed to help with ease of use, or the buttons may lie flat. The overlay 12 may further include a clear covering over the display 22 to aid in scratch protection without impeding the view of the display graphics. It should be understood that this is but one representation of one embodiment of an overlay that may be used in conjunction with the device of the present invention. The present disclosure could be incorporated into a variety of packaging configurations. Preferably, the housing is monogrammed with the owner's name and phone number to ensure quick return if the device is lost. Moreover, the personal caregiver alert device should be portable, such that the device can accompany the caregiver as the caregiver works. The device should be small and lightweight enough to carry in a pocket, or strapped onto a caregiver's arm.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A portable device for coordinating a plurality of time-sensitive tasks with corresponding alarms to alert a caregiver, said device comprising:
   a display,
   a microprocessor capable of monitoring a plurality of functions dedicated to assist said caregiver in managing a plurality of tasks for multiple patients,
   at least one user input feature, and
   at least one alarm capable of alerting said caregiver upon time to perform said task, wherein said device includes a bed assignment mode for programming and updating said caregiver's current bed assignments, a task mode for programming and updating time-sensitive tasks and associating said tasks with at least one current bed assignment, and at least one time clock capable of coordinating a plurality of alarms to one or more bed assignments and associated tasks, wherein one or more of said tasks are custom selected and entered into said device by said caregiver.

2. The device of claim 1, wherein said time-sensitive tasks are pre-programmed into the microprocessor under one or more alert categories, said categories comprising activities of daily living, airway, assessment/act, preventative, and restoratives.

3. The device of claim 1, wherein said bed assignment mode is capable of tracking up to ten (10) separate alerts, respectively for 1 to 4 time sensitive tasks, on up to fifteen (15) bed locations.

4. The device of claim 1, wherein said time-sensitive tasks include , one or more of:
   ambulate, oxygen assessment, meals, ROM, toileting, aerosol, suctioning, tracheal care, phoning a doctor, blood transfusion, fever checks, medicine adjustment, general protocol, vital signs, change dressing, neuro check, pulse check, safety round, service round, skin// turn, and splints.

5. The device of claim 1, wherein said at least one alarm may be set according to:
   a particular time of day using a real-time clock, or
   a specific length of time set forth in time intervals.

6. The device of claim 1, wherein activation of said alarm prompts a display of the protocol required at said bed assignment corresponding to said alarm.

7. The device of claim 6, wherein said default prompt shows "wash hands" and "check patient D." across said display.

8. The device of claim 1, further including at least one USB port to allow interfacing with said microprocessor.

9. A portable device adapted for use by a nursing team, capable of coordinating a plurality of time-sensitive tasks with corresponding alarms to alert a nursing team member, said device comprising:
   a display,
   an microprocessor core capable of monitoring a plurality of functions dedicated to assist said nursing team member in managing a plurality of time-sensitive tasks for multiple patients,
   at least one user input feature, and
   at least one alarm capable of alerting said caregiver upon time to perform said task,
   wherein said device is configured to receive assigned duties from a nursing team leader, said duties including bed assignments and one or more time-sensitive tasks pre-programmed into said microprocessor core under one or more alert categories, said categories comprising activities of daily living, airway, assessment/act, preventative and restoratives, and wherein said device includes a task mode for programming and updating said time sensitive tasks and associating said tasks with at least one current bed assignment.

10. The device of claim 9, wherein said team leader assigns team members tasks by inputting assignments directly onto said team member devices.

11. The device of claim 9, wherein said team member tasks may be downloaded from at least one central site to said team member device.

12. The device of claim 9, wherein said plurality of functions include:
   a bed assignment mode, wherein said team member can designate and update bed numbers,
   a task mode comprising at least one pre-programmed task, wherein said task may be associated with one or more of said bed numbers and continuously updated, and
   at least one time clock capable of coordinating a plurality of alarms to one or more corresponding bed number and associated task.

13. The device of claim 12, said bed assignment mode is capable of tracking up to ten (10) separate alerts, respectively for 1 to 4 time sensitive tasks, on up to fifteen (15) bed locations.

14. The device of claim 9, wherein said tasks, include:

ambulate, oxygen assessment, meals, ROM, toileting, aerosol, suctioning, tracheal care, phoning a doctor, blood transfusion, fever checks, medicine adjustment, general protocol, vital signs, change dressing, nero check, pulse check, safety round, service round, skin/turn, and splints.

15. The device of claim 9, wherein said at least one alarm may be set according to:

a particular time of day using a real-time clock, or to a specific length of time set forth in time intervals.

16. The device of claim 9 wherein one or more of said tasks are custom selected and entered into said device by said nursing team.

17. The device of claim 9, further including at least one USB port to allow interfacing with said microprocessor.

18. The device of claim 9 wherein activation of said alarm prompts a display of the required protocol required at said bed assignment corresponding to said alarm.

19. The device of claim 18 wherein said default prompt shows "wash hands" and "check patient I.D." across said display.

* * * * *